United States Patent [19]

Fung et al.

[11] Patent Number: 5,245,015
[45] Date of Patent: Sep. 14, 1993

[54] MONOCLONAL ANTIBODIES WHICH NEUTRALIZE HIV-1 THROUGH REACTION WITH A CONFORMATIONAL EPITOPE IN VITRO

[75] Inventors: Michael S. C. Fung, Houston; Bill N. C. Sun; Cecily R. Y. Sun, both of Bellaire, all of Tex.

[73] Assignee: Tanox Biosystems, Inc., Houston, Tex.

[21] Appl. No.: 692,299

[22] Filed: Apr. 26, 1991

[51] Int. Cl.$^5$ .................. A61K 39/21; C12N 15/12; C12N 5/20

[52] U.S. Cl. ................ 530/388.35; 530/389.4; 530/809; 530/866; 530/388.3; 530/23.53; 435/69.6; 435/240.27; 435/172.2; 424/85.8; 424/86; 935/15; 935/95

[58] Field of Search .......... 435/69.6, 188.5, 172.2, 435/240.27; 530/388.35, 389.4, 388.3, 809, 866; 935/15, 95; 424/85.8, 86

[56] References Cited

U.S. PATENT DOCUMENTS 4,772,547 9/1988 Heimer .................... 435/5

OTHER PUBLICATIONS

Robinson et al. AIDS Research and Hum. Retro. 6(5): 567-579 (May 1990) "Id. of Cons. and Variant Epit. of HIV-1 gp. 120 by Human Malo prod. by EBV trans. cell lines".

Posner et al., J. of Imm., 146:4325-4333, (May 16, 1991) "An IgG Hum. Mab that reacts w/HIV-1/gp 120, inhib. virus binding, and neutralizes infection".

Fung et al., J. of Virology 66(2):848-856 (1992).

Ho et al., PNAS 88:8949-8952 (1991).

Lerner et al., Advances in Immunology 36:1-44 (1984) Antibodies of Predetermined Specificity in Biology and Medicine.

Primary Examiner—David L. Lacey
Assistant Examiner—T. Michael Nisbet
Attorney, Agent, or Firm—Eric P. Mirabel

[57] ABSTRACT

The monoclonal antibodies (mAbs) of the invention bind to a neutralizing epitope on the gp120 glycoprotein of HIV-1. The binding seems to be conformation-dependent, in the sense that altering the conformation of gp120 (by deglycosylating the gp120, by reducing the cysteine bonds in the peptide backbone) will inhibit the binding. The mAbs of the invention are group specific and can neutralize different strains and different isolates of HIV-1. The binding of these mAbs to gp120 is enhanced by the binding of other antibodies to the principal neutralizing determinant (amino acid residue numbers 296-331) of gp120.

3 Claims, 5 Drawing Sheets

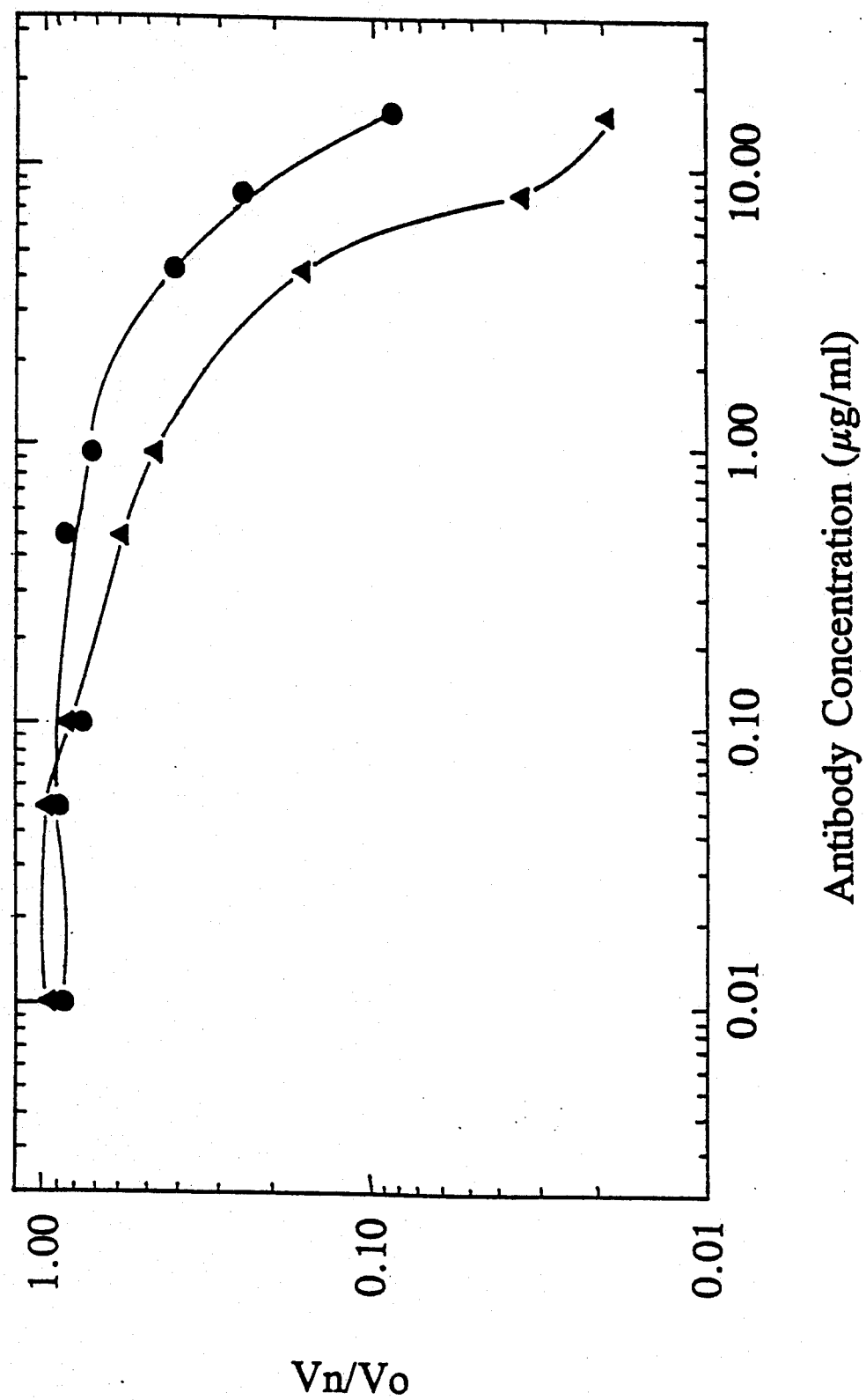

sCD4 (μg/ml)

MONOCLONAL ANTIBODIES WHICH NEUTRALIZE HIV-1 THROUGH REACTION WITH A CONFORMATIONAL EPITOPE IN VITRO

FIELD OF THE INVENTION

The invention relates to monoclonal antibodies which bind to an epitope on the external envelope protein of HIV-1 gp120 in a conformation-dependent fashion and which neutralize HIV-1.

BACKGROUND OF THE INVENTION

Acquired Immune Deficiency Syndrome, generally known by its acronym AIDS, is probably the most serious health threat confronting society. It could reach epidemic proportions in the general population before the end of this century. The disease runs a painful and debilitating course and results in the death of its victim. In fact, from diagnosis, the average life span of an AIDS victim is only about three to five years.

HIV-1 also causes a somewhat less serious immunodeficiency syndrome known as AIDS-related complex (ARC). ARC often precedes the onset of AIDS. There are currently many more ARC cases than there are AIDS cases. As the number of infections continues to increase, ARC has, in itself, become a costly and serious health care problem.

AIDS is caused by a virus which has at various times been called human T-cell lymphotropic virus type III (HTLV-III), lymphoadenopathy-associated virus (LAV), and is currently known as human immunodeficiency virus type 1 (HIV-1). Several strains of the virus are known to exist, and it is widely believed that as the virus continues to mutate, many more strains will result.

AIDS results because infection with HIV-1 depletes T helper/inducer lymphocytes (hereinafter referred to as "T cells"). T cells are essential because they control the production of antibodies by the B cells, the maturation of cytotoxic T lymphocytes (killer T cells), the maturation and activity of macrophages and natural killer cells, and, directly and indirectly, numerous other regulator and effector functions of the immune system. Therefore, HIV-1 infection severely compromises the immune response, leaving the victim unable to defend against secondary opportunistic infections. It is often the secondary infections which debilitate the victim and cause death.

In addition to their susceptibility to secondary infections, AIDS victims frequently develop otherwise rare conditions. A large number develop a rare form of skin cancer known as Kaposi's sarcoma.

Infection of a T cell with HIV-1 follows from interaction between an epitope borne by HIV-1 and a receptor site which is located on the T cell surface, known as the CD4 antigen. The epitope on HIV-1 is borne by the envelope glycoprotein gp120 (molecular weight 120,000 daltons). The glycoprotein gp120 is produced when a precursor glycoprotein gp160 is cleaved apart into gp41 (molecular weight 41,000 daltons) and gp120.

HIV-1 is a retrovirus. After the virus has entered the cell, the viral enzyme known as reverse transcriptase transcribes the viral genomic RNA into DNA in the host cell nucleus. The newly synthesized DNA is incorporated into the host cell genome under a variety of activation conditions, and the infected T cell begins to transcribe the new DNA to make copies of messenger RNA and genomic RNA. The viral genomic RNA's are packed with core proteins, reverse transcriptase, and certain other proteins. They are then enveloped by parts of the cellular membrane and budded off from the cell as newly synthesized virions.

These newly synthesized virions can bind to the CD4 antigen on other T cells and enter and infect them. However, HIV-1 can also be transmitted to other T cells through direct cell-to-cell contact or fusion.

Direct cell-to-cell transmission occurs when an infected cell, which expresses the viral gp120 on its surface, binds with the CD4 antigen of an uninfected cell or cells. As a result, the cells fuse and virions can pass to the uninfected cell(s).

Direct cell-to-cell contact and the resulting fusion are a significant source of cellular infection, and may be a major mechanism of T cell destruction in HIV-1 infected individuals. Infected and uninfected cells often fuse in large groups, thereby forming multi-nucleated aggregates known as syncytia. The cell fusion causes the death of cells in the syncytia. See Lifson et al. "Induction of CD4-Dependent Cell Fusion by the HTLV-III/LAV Envelope Glycoprotein", *Nature* 323:725-27 (1986).

Monoclonal antibodies are secreted by hybridoma cells derived from single cell cloning of fused cells. Cells from the monoclonal parent are identical. Accordingly, all the hybridomas of the same clone produce antibodies of the same idiotype which bind to the same epitope of a particular antigen.

Monoclonal antibodies which neutralize HIV-1 are expected to be useful for treatment of HIV-1 infected patients. Such monoclonal antibodies inhibit infection of target cells by free virions and also inhibit syncytium formation between HIV-1-infected cells and other CD4-bearing cells. It is preferred if such monoclonal antibodies can neutralize different strains and isolates of HIV-1.

Passive immunization with neutralizing monoclonal antibodies is expected to be especially effective for uninfected people who are in high-risk groups, and for patients with early-stage infection. Administration of the neutralizing antibodies may either prevent infection by the virus, or may slow the progression of the disease.

SUMMARY OF THE INVENTION

The monoclonal antibodies (mAbs) of the invention bind to a neutralizing epitope on the gp120 glycoprotein of HIV-1 in a conformation-dependent manner. Altering the conformation of gp120 will affect antibody binding. These mAbs are broadly reactive and can neutralize different strains and different isolates of HIV-1, and can inhibit HIV-1 infection of T cells in vitro.

These mAbs can be used as whole antibodies or as antibody fragments or they can be conjugated to cytotoxic or antiviral agents, or to microcarriers which contain such agents, in order to target the delivery of these agents to infected cells. The targeted delivery of therapeutic agents can also possibly be achieved with bispecific antibodies derived from the anti-HIV-1 antibodies of this invention which have been provided with a second specificity for the agent to be delivered to the target. Polyclonal or monoclonal anti-idiotype antibodies against the paratope of the mAbs of the invention can be used to stimulate a neutralizing immune response against HIV-1 in vitro.

The mAbs and anti-idiotypes of this invention can be used as antibodies derived wholly from mice or other animals. Alternatively, the mAbs and anti-idiotypes can be made in the form of whole human antibodies, animal/human chimeric antibodies, single-chain antibodies, or antibody fragments. For the chimeric antibodies, the constant region is human-derived, and the variable region (or only the antigen binding region) is animal-derived.

This invention also pertains to native or recombinant proteins or their fragments which contain the binding epitope recognized by the mAbs of this invention. The proteins can also be used to detect neutralizing antibodies against HIV-1 in a biological fluid.

BRIEF DESCRIPTION OF THE DRAWINGS

FIG. 2A shows a syncytium-forming assay where G3-4 was tested for neutralization of HIV-$1_B$ (filled circles) and HIV-$1_{RF}$ (filled triangles), with Vn/Vo representing the ratio of the number of virus induced syncytium-forming units ("SFUs") in the test wells with antibody, to the total number of virus induced SFUs in the control when the growth medium alone was added.

DESCRIPTION OF THE PREFERRED EMBODIMENTS

A. Summary of Procedures Used

Figure 1:
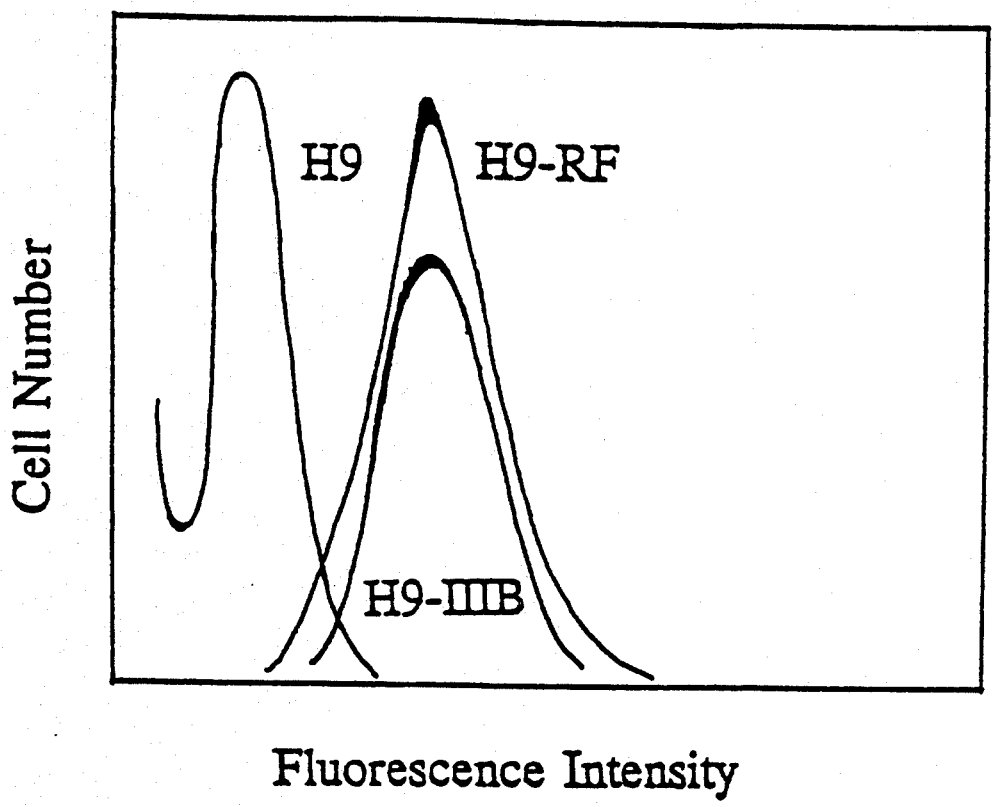
FIG. 1 shows the binding of G3-4 to H9 cells infected with HIV-$1_B$ or HIV-$1_{RF}$ by flow cytometry.

The monoclonal antibodies of the invention bind to the HIV-1 viral envelope glycoprotein gp120. In the processing of HIV-1 specific envelope protein in infected T cells, gp41 is a transmembrane protein and is largely not exposed. In contrast, gp120 is an external envelope protein which is extracellular. Thus, in infected T cells the gp120 protein offers binding epitopes for the mAbs of the invention.

More specifically, the mAbs of the invention include mAbs which bind to a neutralizing epitope in a conformation-dependent fashion, i.e., when the gp120 conformation is altered, the antibody binding is affected. The mAbs of the invention were found to be effective in inhibiting HIV-1 infectivity in vitro. Importantly, these mAbs can neutralize different strains and different isolates of HIV-1 (i.e., they are broadly reactive).

The mAbs of this invention have high potency in neutralizing infectivity. For example, they inhibit HIV-$1_B$ with an $IC_{50}$ of 3.6 $\mu$g/ml and HIV-$1_{RF}$ with an $IC_{50}$ of 0.92 $\mu$g/ml. The findings from cell staining studies by flow cytometry show that the binding of the mAbs of the invention to gp120 seems to be enhanced by an antibody which binds to an epitope on the principal neutralizing determinant ("PND") of gp120. This indicates that a particularly preferred embodiment may involve combining the mAbs of the invention with the antibodies which bind to the PND. The PND is the peptide segment on gp120 from amino acid residue numbers 296 to 331, as determined from the gp120 sequence of the HIV-$1_B$, or sequences of the corresponding regions from other HIV-1 strains. See Devash, Y., Proc. Nat'l Acad. Sci. USA 87:3445-3449 (1990). The PND peptide segment is in the relatively variable region, V3, of gp120. However, recent studies indicate that there are conversed features in the PND segment. The amino acid sequences of PND segments in field HIV-1 isolates from patients are closely related. See LaRosa, G. J. et. al., Science 249:932-935 (1990). Antibodies which target the PND may be effective in inhibiting HIV-1 infection of the homologous virus against which the antibodies were raised.

The mAbs of the invention, bind to a conformational epitope on gp120, and therefore the amino acid sequence cannot be determined, as these mAbs will not bind to a synthetic peptide.

One preferred mAb of the invention is G3-4, which binds to a unique site on gp120 as tested by ELISA. Its binding is not inhibited by BAT123, which recognizes an amino acid sequence within the PND (amino acid residue numbers 296-331). Its binding is also not inhibited by G3-519, which recognizes the CD4-binding domain (amino acid residue numbers 412-456). However, its binding to gp120 can be inhibited by sCD4, indicating that G3-4 may recognize a confomational epitope involved directly or indirectly in CD4-gp120 interaction. The hybridomas which produce the mAb G3-4 are on deposit at the American Type Culture Collection, 12301 Parklawn Drive, Rockville, Md., 20852, under Accession No. HB10733.

Suitable mAbs of the invention, including G3-4, are produced by first immunizing an animal, preferably a mouse, with a suitable antigen, which in this case was gp120 purified from the lysates of infected cells. The antigen can, however, be in whole form, e.g., whole HIV-1 virions, or cells infected with a virus and expressing the virus or its antigenic domains can also be used.

The antigenic domains of HIV-1 on gp120, or synthetic or recombinant peptides which have the same or an immunologically equivalent sequence to these antigenic domains can also be used, provided that the conformation is maintained. These synthetic or recombinant peptides for use in immunization can be synthesized by conventional techniques, such as with the RaMPS system (DuPont DeNemours & Co.), which applies Fmoc chemistry. Alternatively, recombinant peptides containing these peptides may be biosynthesized by expressing in E. coli or eukaryotic cells the gene segments containing the appropriate coding sequences.

When using a synthetic peptide segment or a short recombinant peptide as an immunogen, it is usually more effective to conjugate it to a protein carrier, for example, HBsAg, hepatitis B virus core antigen, ovalbumin, bovine serum albumin, or preferably keyhole lympet hemocyanin ("KLH"). Once again, the protein carrier must not alter the conformation of the peptidic segment. If the peptidic segment lacks a lysine residue or if the lysine residue is in the middle part of the segment, it is desirable to add a lysine residue at the C-terminal end. Because the N-terminus already has an α-amino group, the modified synthetic peptide will have two available amino groups for linking.

Multiple molecules of peptides can be conjugated to each molecule of the carrier to make the immunogen. With KLH, a preferred molar ratio for peptide/KLH is 10. The conjugation can be done with well established methods using glutaraldehyde or bis (sulfosuccinimidyl) suberate or preferably disulfosuccinimidyl tartrate as the cross-linkers.

One immunization protocol for preparing the mAbs is to inject into each mouse 50 μg of the conjugate of KLH and the aforementioned recombinant or synthetic peptides in Freund's complete adjuvant. Two and four weeks later, the same amount of antigen is given subcutaneously in Freund's incomplete adjuvant. After about six weeks, the fourth antigen injection is given intraperitoneally in saline. Mice are sacrificed 4 days after the last injection and the spleens (or sometimes the lymph nodes) are removed for preparing single cell suspensions for fusion with myeloma cells.

Lymphocytes from the spleens (or lymph nodes) which have been removed from the mice can be fused with myeloma cells to prepare hybridomas secreting the mAbs of the invention. The fusion procedure with polyethylene glycol and other various procedures concerning the cloning and the culturing of hybridomas have been well established. One preferred protocol is the well-known one described by Hudson, L. and Hay, F. C. (Practical Immunology, 2nd edition, pp. 303–313, 1980, Blackwell Publishing Co., Boston), in which the lymphocytes are fused with non-secreting mouse myeloma cells, such as NS-1 or Sp2/0 cells, using polyethylene glycol. The fusion reagent used to make G3-4 was polyethylene glycol mixed with dimethyl sulfoxide (DMSO) in calcium magnesium-free phosphate buffered saline (PBS).

Reagents other than those discussed can be used for the chemical fusion. Another alternative is to use electrical fusion rather than chemical fusion to form hybridomas. This technique is well-established. Instead of fusion one can also transform a B-cell to make it immortal using, for example, an Epstein Barr Virus or a transforming gene. (For a method of transforming a B-cell, see "Continuously Proliferating Human Cell Lines Synthesizing Antibody of Predetermined Specificity," Zurawski, V. R. et al, in *Monoclonal Antibodies*, ed. by Kennett R. H. et al, Plenum Press, N.Y. 1980, pp 19–33.)

The screening of hybridomas for monoclonal antibodies reactive with the immunogen can be performed with an enzyme linked immunosorbent assay (ELISA). Because one is screening for a conformational epitope, one generally will use purified native gp120 as the solid-phase antigen. This preparation of gp120 is glycosylated and non-reduced in order to retain the disulfide bridges. The specific procedure used in generating the mABs of the invention is described below under Heading "1".

Generally, the mABs which are first obtained will be murine-derived, and thus may be immunogenic or allergenic. It is therefore desirable to produce chimeric antibodies (having an animal variable region and a human constant region), or to use human expression vectors (Stratagene Corp., La Jolla, Calif.) to produce fragments of human antibodies ($V_H$, $V_L$, $F_V$, Fd, Fab, or $F(ab')_2$) and then construct whole human antibodies using techniques similar to those for producing chimeric antibodies. In addition, one can create antibodies in which the entire constant portion and most of the variable region is human-derived, and only the antigen binding site is derived from some other mammals. See Riechmann, L. et al., Nature 332:323–327 (1988). Further, one can create single-chain antibodies in which the heavy and light chain $F_v$ regions are connected. See Huston, J. S. et al., Proc. Natl. Acad. Sci. USA 85:5879–5883 (1983).

All of the aforementioned human and humanized antibodies are less immunogenic than other mammalian equivalents, and the fragments and single-chain antibodies are less immunogenic than whole antibodies. All these types of antibodies are therefore less likely to evoke an immune or allergic response.

MAbs of the invention can possibly be used to reduce or eliminate the virus infected T cells by antibody-dependent cellular cytotoxicity (ADCC), complement-mediated cytolysis, or other cytolytic or regulatory immune mechanisms. For example, antibodies of certain IgG subclasses, such as mouse $IgG_{2a}$ and human $IgG_1$ and $IgG_3$, might mediate ADCC carried out by certain Fc receptor-bearing phagocytic leukocytes. Administration of such mouse $IgG_{2a}$ antibodies, chimeric antibodies bearing human γ-1 or γ-3 chains, or human $IgG_1$ or $IgG_3$ antibodies might be used to down-regulate or lyse infected T cells.

The mAbs of the invention can also be used for targeting cytotoxic agents to HIV-1-infected cells in vitro. The mAbs of the invention can also be used as carrier agents of cytotoxic drugs or for delivering an effector substance, by conjugating the mAbs to these substances. A toxin-antibody conjugate will bind and directly kill infected T cells. These toxins are cytolytic or cytotoxic agents, including cytotoxic steroids, gelonin, abrin, ricin, Pseudomonas toxin, diphtheria toxin, pokeweed antiviral protein, tricathecums, radioactive nuclides, and membrane-lytic enzymes (such as phospholipase).

The antibody and the agent can be conjugated by chemical or by genetic engineering techniques. The toxin-antibody conjugates may be used alone or in combination with the free antibodies of the invention.

The antibodies of the invention (and the toxin conjugates, fragments, and other derivatives) are administered systemically, and preferably intravenously. They can be administered in any pharmaceutically acceptable vehicle.

Another therapeutic alternative involves active immunization, wherein antibodies specific to the epitope bound by the mAbs of the invention are endogenously produced in vivo. These endogenously produced antibodies bind to this epitope and cause destruction of the infected T cells. Production of such antibodies can be induced either by administering an immunogenic peptide, e.g., a recombinant peptide, containing the same sequence (or an immunologically equivalent sequence) as the epitope bound by the mAb of the invention.

Production of such antibodies can also be induced by administering a paratope-specific anti-idiotypic antibody. Anti-idiotype antibodies against the paratope of the antibodies of the invention bear the internal image of the gp120 epitope. These anti-idiotypic antibodies may possibly be used for active immunization to induce the endogenous formation of antibodies against these epitopes.

Such paratope-specific anti-idiotypic antibodies are administered to a patient in an immunogenic amount sufficient to induce the formation of antibodies against infected T cells. These anti-idiotypic antibodies are preferably administered as human or humanized antibodies, or single-chain antibodies, to minimize any immune response against them. They may also be any of the antibody fragments, $V_H$, $V_L$, $F_V$, Fd, Fab, or $F(ab')_2$.

Certain factors, such as granulocyte monocyte-colony stimulating factor (GM-CSF) or monocyte-colony stimulating factor (M-CSF), are known to induce the proliferation of leukocytes, including those mediating ADCC. In in vitro experiments, GM-CSF and M-CSF have been shown to augment the ADCC activity on tumor cells mediated by monoclonal antibodies specific for surface antigens expressed on the tumor cells. The therapeutic effect of specific mAbs of the invention, conjugates, or polyclonal antibodies in depleting infected T cells could perhaps be enhanced by combining them with factors that augment ADCC activities.

Derivative antibodies can be made which draw cytotoxic cells such as macrophages or cytotoxic T cells toward the targeted T cells. These derivative antibodies include bi-specific antibodies having a specificity for a receptor of a cytotoxic cell and a specificity for the targeted infected T cells. Such hybrid bi-specific antibodies can include two different Fab moieties, one Fab moiety having antigen specificity for the targeted epitopes, and the other Fab moiety having antigen specificity for a surface antigen of a cytotoxic cell, such as CD3 or CD8. The bi-specific antibodies of the invention can be a single antibody having two specificities, or a heteroaggregate of two or more antibodies or antibody fragments. See, e.g., C. Reading, U.S. Pat. Nos. 4,474,893 and 4,714,681; Segal et al., U.S. Pat. No. 4,676,980.

While mAbs of the invention may possibly be used for in vivo applications, they may also be used in extracorporeal ex-vivo applications. The infected T cells in the circulation of the patients might be removed by an affinity matrix (antibody immobilized on a solid phase) which is conjugated with the mAbs of the invention.

Another use for the mAbs of the invention is for determining numbers and relative proportions of infected T cells. The mAbs of the invention can be used in an assay in which infected T cells are bound and their relative numbers are determined. This could be useful in indicating the patients' disease status.

For such an assay, the mAbs of the invention can be used in standard assays which are used to determine cell surface antigens. In general, the mAbs are allowed to bind to the infected cells in the leukocyte sample. The detection of the binding can be accomplished by conventional cell staining procedures, for example, a fluorescently labeled second antibody can be used to detect binding of antibody.

The invention will now be further described with reference to specific examples.

B. Production and Testing of G3-4 Monoclonal Antibodies

1. Antibody Production and Screening

The envelope glycoprotein, gp120, of HIV-$1_B$ was prepared from H9/HIV-$1_B$ cell extracts. H9/HIV-$1_B$ cells were lysed with a lysing buffer consisting of 10 mM Tris-HCl, pH 7.5, 120 mM NaCl, 1 mM $MnCl_2$, 0.5% Triton X-100 and 0.1 mM phenylmethyl sulfonyl fluoride. The extracts were heat-inactivated for 1 hour at 56° C. and reacted with lentil-Sepharose (Sigma, St. Louis, Mo.). The bound fraction was eluted and incubated with Affigel-10 coupled with a murine monoclonal antibody against gp120 (BAT123). See Fung et al. Biotechnology, 5:940-946 (1987). The viral gp120 fraction was eluted and used as the immunogen. Five male BALB/c mice were immunized with 25 μg of protein in Freund's complete adjuvant and three subsequent immunizations of 25 μg in the same adjuvant at 1-month intervals. Three days after the final booster immunization, the mice were sacrificed and spleen cells were isolated and fused with Sp2/0 myeloma cells as described by Fung et al., (supra). Hybrids were selected by supplementing the growth medium with 0.1 mM hypoxanthine, 0.4 μM aminopterin and 16 μM thymidine. Two weeks later, supernatants were collected from the wells of the microtiter plates. Each well had about 10 hybrid colonies after 10 days. There were estimated to be about 140,000 hybridomas for consecutive screening by ELISA with the purified HIV-1 gp120 as coating antigens.

Mab from hybridomas selected for further characterization were produced in mouse ascites and purified by protein A affinity chromatography. The outgrowths giving the strongest positive reactions in both screening assays were single-cell cloned by limiting dilution, and the supernatants were screened by ELISA using gp120 as the coating antigen. One of these mAbs was the G3-4 mAb.

2. Radioimmunoprecipitation Assay ("RIPA") to Determine the Binding Site, the Effect of Disulfide Bond Reduction, and the Effect of De-Glycosylation on Binding A RIPA was run to determine the binding site of G3-4 on solubilized HIV-1 gp120, and whether reducing the disulfide bonds in gp120 and de-glycosylating gp120 would affect the binding of the G3-4 antibody. The procedure was carried out as follows.

H9 cells (infected with HIV-$1_B$ or HIV-$1_{RF}$) were metabolically labelled for 4 hours with [$^{35}$S] cysteine and [$^{35}$S] methionine (100 μCi/ml) (ICN, Irvine, Calif.). The cells were washed with basal medium RPMI-1640, and then suspended in a RIPA lysing buffer (50 mM Tris-HCl, pH 8.0, 150 mM NaCl, 1% Triton X-100, 1% Na deoxycholate, 0.1% SDS, and 1 mM phenylmethyl sulfonyl fluoride). Lysates were precleared with protein A-Sepharose bound to rabbit antiserum to mouse κ light chain (κ-PAS) for 3 hours at room temperature. RIPA was performed by adding 3 μg purified Mab G3-4, 0.2 ml of 10% suspension of κ-PAS to 200 μl of labelled and clarified lysate. The samples were incubated for 18 hours at 4° C. and the beads were washed with the RIPA lysing buffer. The pellets were suspended in electrophoresis sample buffer and boiled for 3 minutes. Proteins were analyzed by SDS-polyacrylamide gel electrophoresis followed by autoradiography.

To study of the effect of conformation of gp120 on its binding to G3-4, the disulfide bridges of the solubilized [$^{35}$S]-gp120 were reduced by dithiothreitol ("DTT") before incubation with G3-4.

To study the effect of de-glycosylation, infected H9 cells were incubated with a glycosylation inhibitor, tunicamycin, to block the glycosylation of gp120. Cells were then labeled with [$^{35}$S]-methionine and the RIPA was performed. Alternatively, to study de-glycosylation, metabolically labeled cell lysates were treated with a glycosidase, Endo H.

It was found in the RIPA that G3-4, like AIDS patient sera, precipitated specifically both gp120 and gp160 of HIV-1$_B$ and HIV-1$_{RF}$. G3-4, however, did not bind to gp120 and gp160 of HIV-1$_B$ reduced by DTT. Pre-treatment of infected H9 cells with tunicamycin or pre-treatment of the cell lysates with Endo H also abolished the binding between G3-4 and gp120. In contrast, treatment of gp120 and gp160 with DTT and tunicamycin did not affect the binding of polyclonal AIDS patient immunoglobulins. These results suggest that G3-4 may recognize a conformational domain of gp120 which is made up of glycosidic moieties and disulfide linkages.

3. Immunofluorocytometric Analysis of the Binding of G3-4 and G3-136 to HIV-1-Infected H9 cells The binding of purified G3-4 to H9 cells infected by HIV-1$_B$ and HIV-1$_{RF}$ was analyzed by flow cytometry. Uninfected and HIV-1-infected H9 cells were grown in log phase and washed twice in PBS containing 1% BSA and 0.05% sodium azide at 4° C. The cells were resuspended at $1 \times 10^7$ cells/ml in the same buffer. Fifty μl of the cell suspension were incubated with 10 μg/ml of the antibody in the same buffer at 4° C. for 30 minutes. 4 ml of the buffer was then added to the tube. The cells were centrifuged at 300×g for 5 minutes. The supernatant was discarded by aspiration, and the cell pellet was resuspended in 50 μl of the buffer. Fifty μl of a pre-titered fluorescein conjugated goat anti-mouse F(ab')$_2$, (1:10 dilution) (Cappel) were added to the cells. The cells were incubated for 30 minutes at 4° C., washed with 4 ml of the buffer and fixed with 0.5 ml 1% paraformaldehyde and analyzed with a Coulter EPIC cell analyzer.

In the study of the effect of other anti-HIV-1-gp120 mAb on the binding of G3-4 and G3-136 to HIV-1$_B$-infected H9 cells, diluted biotinylated G3-4 or G3-136 was used at a dilution of 1:1000. 10 μg/ml of either chimeric BAT123, G3-472, G3-4, G3-136, or G3-519 was added together with the biotinylated G3-4 or G3-136 for incubation at 4° C. for 30 minutes. For controls, no competing mAb was added. The negative control contained an irrelevant murine mAb IgG$_1$: i.e., MOPC21.

G3-4 was shown to bind specifically to H9 cells infected with HIV-1$_B$ (92.3%) and HIV-1$_{RF}$ (99.3%). See FIG. 1. In an assay to study the effect of the other mAb on the binding of G3-4 and G3-136, it was shown that their binding to HIV-1-infected H9 cells was enhanced by chimeric BAT123 and G3-472, which recognize the PND in the V3 domain of gp120 (Table I).

4. HIV-1 Neutralization by G3-4

HIV-1 neutralization studies were performed by a syncytium-forming assay using CEM-SS cells. Two-fold serial dilutions of purified G3-4 were made in RPMI-1640 medium supplemented with 10% heat-inactivated fetal bovine serum. Fifty μl of G3-4 were mixed with an equal volume of virus (100 syncytium-forming units ("SFUs")) and incubated for 1 hour at room temperature. The mixtures were added into two poly-L-lysine treated microtiter wells containing $5 \times 10^4$ DEAE-dextran treated CEM-SS cells, and incubated for 3-4 days. The number of syncytia formed were counted using an inverted microscope. The neutralization titers were determined by using a 50% (Vn/Vo=0.5) neutralization point, as shown in FIG. 2A. Vn represents the number of virus-induced SFUs in the test wells and Vo the number of virus induced SFUs in the control when growth medium alone was added. G3-4 neutralized both HIV-1$_B$ (IC$_{50}$=3.6 μg/ml, IC$_{90}$=14 μg/ml) and HIV-1$_{RF}$ (IC$_{50}$=0.92 μg/ml, IC$_{90}$=7.4 μg/ml).

5. Neutralization Assay of HIV-1 Clinical Isolates in the Infection of PHA-Activated Peripheral Blood Mononuclear Cells (PBMC)

PBMC were isolated from HIV-1-seronegative donors by density-gradient sedimentation using Ficoll-Hypaque. The PBMC were stimulated with 2 μg/ml phytohaemagglutinin (PHA) in RPMI-1640 medium containing 15% heat-inactivated fetal bovine serum and 20 units/ml interleukin 2. After 3 days of incubation at 37° C. and 5% CO$_2$, the cells were washed in RPMI-1640 medium containing 15% heat-inactivated fetal bovine serum as the washing medium. The cells were resuspended at a density of $2 \times 10^6$ cells/ml in RPMI-1640 containing 15% heat-inactivated fetal bovine serum and 40 units/ml of interleukin 2 (as the complete growth medium). Clinical HIV-1 (LS, PR, AC, JR-CSF, MU, L, CO, JR-FL and B) were isolated from the plasmas or PBMC of HIV-1-infected individuals. They were propagated in PHA-activated normal PBMC, and culture supernatants of these clinical HIV-1 isolates were titered and kept at −80° C. for use in a neutralization assay by mAb G3-4.

In the neutralization assay, 500 μl of viral supernatants of these clinical HIV-1 isolates containing 50 TCID$_{50}$ was incubated with 500 μl of different dilutions of G3-4 (100 μg/ml to 20 ng/ml) for 1 hour at 37° C. in a 24-well culture plate. After the incubation, 1 ml of the pre-washed PHA-stimulated PBMC ($2 \times 10^6$/ml) was added to each of the wells containing the virus-antibody mixture or virus plus equivalent volume of plain culture medium (as control). After 24 hours of incubation at 37° C. and 5% CO$_2$, the plates were centrifuged at 300× g for 7 minutes and the supernatant from each well was carefully discarded by aspiration. The cells were then resuspended in the washing medium as before. The washing procedure was repeated one more time, and finally the cells were incubated in 2 ml of the complete growth medium. The cultures were then maintained at 37° C. and 5% CO$_2$ for 7 days. Culture supernatant was then collected for assay of HIV-1 antigens by the Abbott HIV-1 antigen assay kit. The degree of neutralization by G3-4 was expressed as the percent decrease in the HIV-1 antigen concentration in the test wells as compared with the control wells (without G3-4).

Figure 2B:
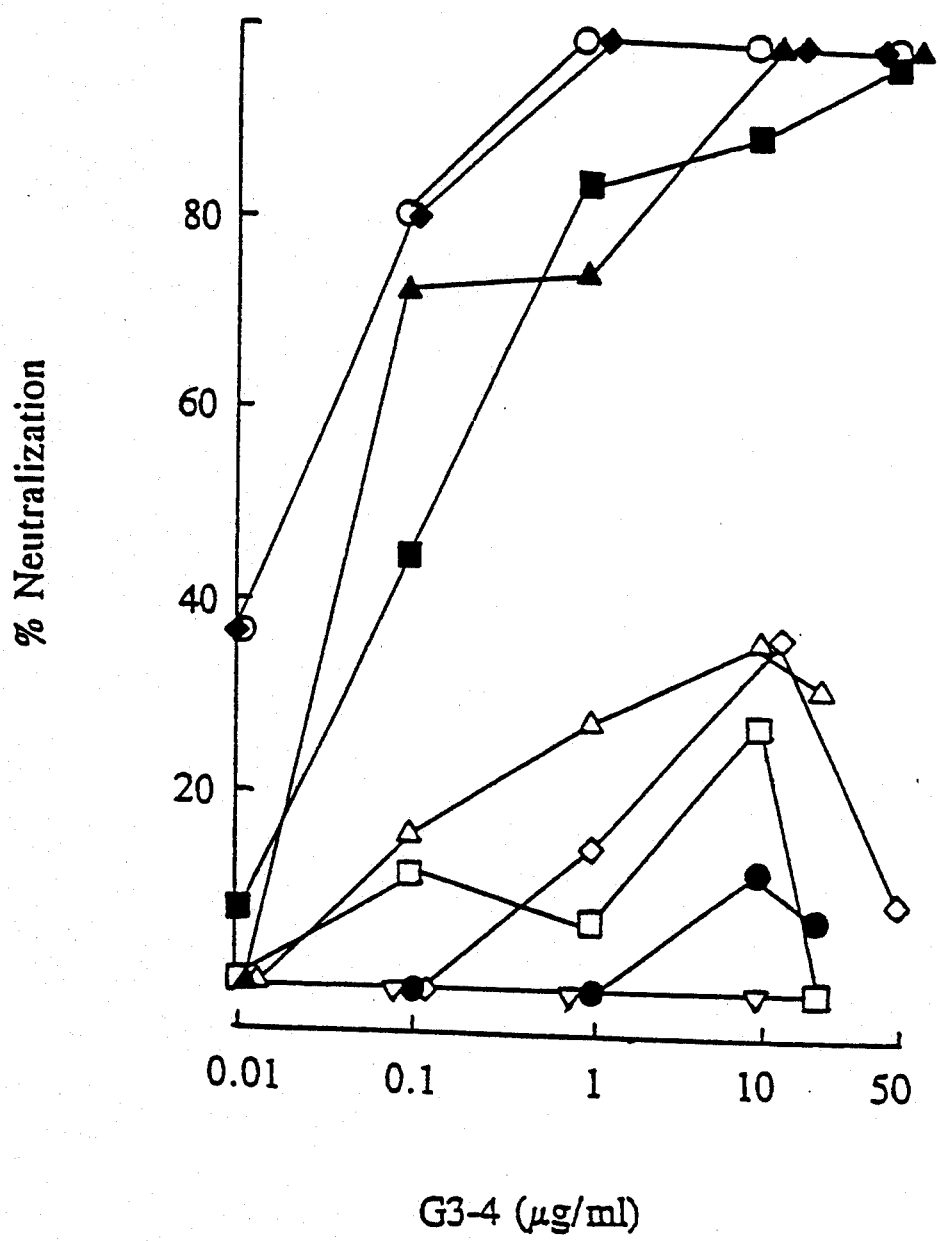
FIG. 2B shows the neutralization of HIV-1 clinical isolates by G3-4 in the infection of PHA-activated peripheral blood mononuclear cells. The HIV-1 isolates include LS (open circles), PR (closed diamonds), AC (closed squares), JR-CSF (closed triangles), MU (open triangle), L (open diamond), CO (open square), JR-FL (open inverted triangle), and B (closed circle).
Figure 3:
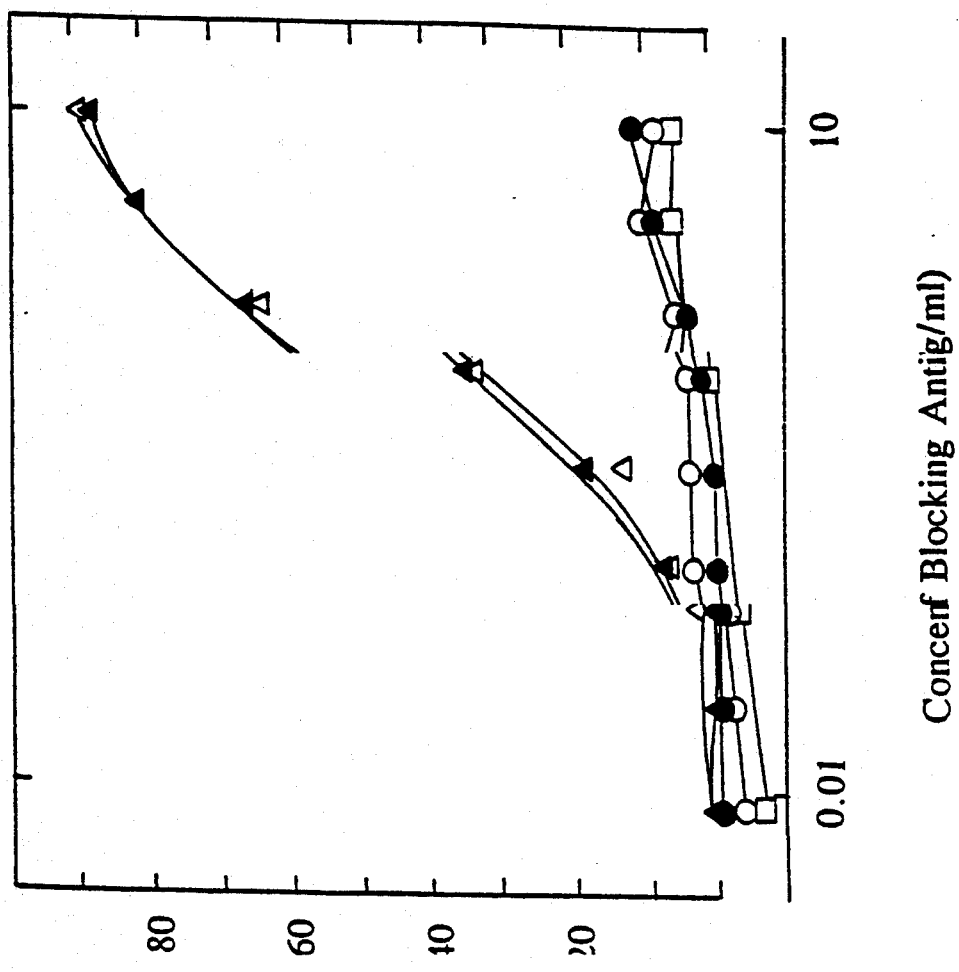
FIG. 3 shows the inhibition of the binding of biotinylated G3-4 to solid-phase purified HIV-$1_B$ gp120 by G3-136 (open triangles). Other monoclonal antibodies tested include BAT123 (open circles), G3-519 (filled circles), irrelevant murine IgG1 (open square) and G3-4 (filled triangles).
Figure 4:
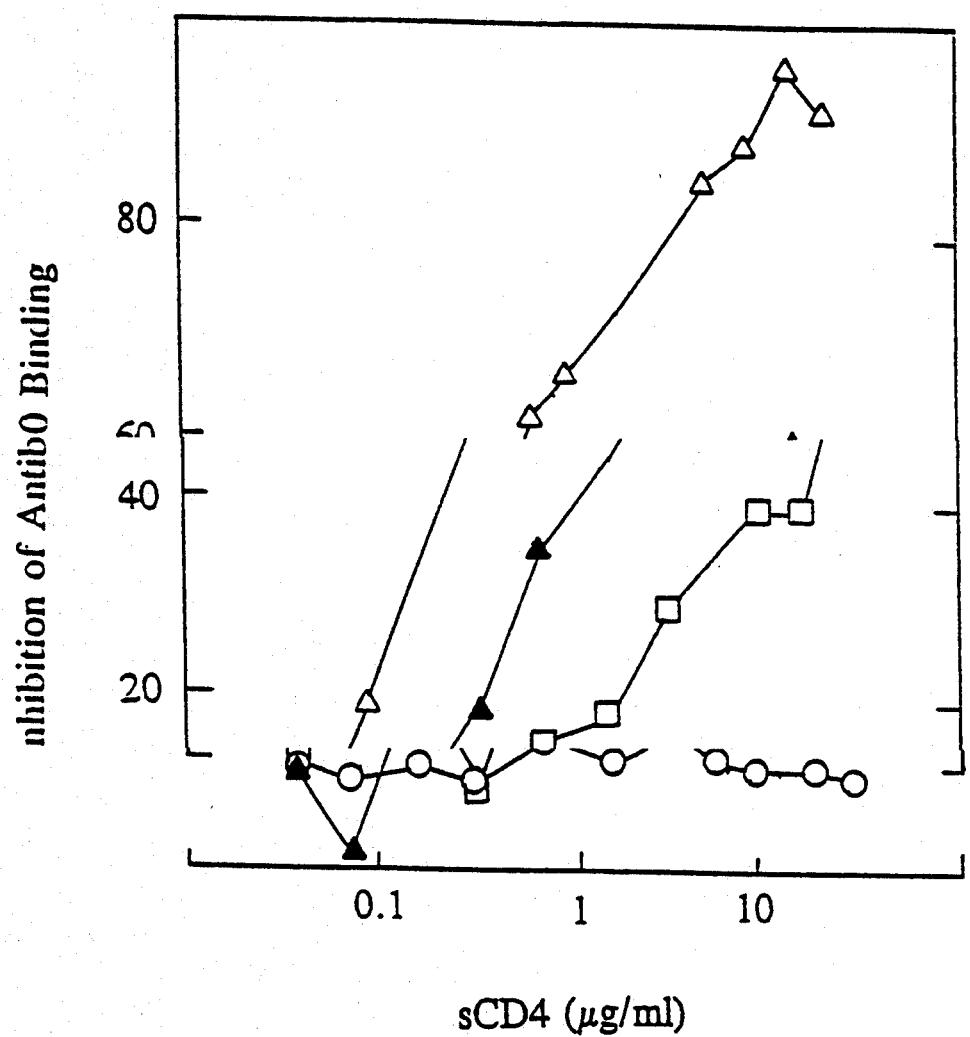
FIG. 4 shows the inhibition of the binding of biotinylated G3-4 to captured purified HIV-$1_B$gp120 by recombinant soluble CD4 (sCD4). The biotinylated antibodies tested include BAT123 (open circles), G3-472 (filled circles), G3-4 (open triangles), G3-136 (filled triangles) and G3-519 (open squares).

Of the nine primary HIV-1 isolates tested, G3-4 neutralized four (PR, LS, AC, and JR-CSF) with IC$_{90}$ (concentration of the antibody required for 90% inhibition of HIV-1 infection) ranging from 0.3 μg to 10 μg (FIG. 2B). The remaining five HIV-1 isolates require up to 20 μg of G3-4 to achieve more than 50% neutralization.

6. Epitope Mapping Using a Competition ELISA

An attempt was made to determine the epitope to which G3-4 bound, using an ELISA in which G3-4 was competed against five other anti-HIV-1 gp120 mAb. The procedure was carried out as follows.

Immunlon 2 microtest plates were coated with 50 μl of 0.5 μg/ml purified HIV-1$_B$ gp120 in phosphate-buffered saline (PBS) and incubated overnight at room temperature. 200 μl of 5% non-fat dry milk in PBST (PBS with 0.02% Tween 20) was then added to each well to block the remaining binding sites, and the wells were incubated for 1 hour at room temperature. At the end of the blocking step, the plates were washed four times with PBST. 50 µl of PBSTB was then added to each well. 50 µl of 20 µg/ml of G3-4 and the relevant control antibody was added to the duplicate wells in the first column of the plate. The solutions were then serially diluted to the eleventh column. 50 µl of PBSTB was added to the wells in the twelveth column. 50 µl of the diluted biotinylated mAb (either BAT123, G3-136, G3-4, G3-519 or G3-472) was then added to the corresponding wells for 1 hour at room temperature. The dilution of each test biotinylated mAb was pre-determined to give approximately 80% of maximal binding to the solid-phase HIV-1$_B$ gp120. The plates were then washed as before. 100 µl of diluted streptavidin conjugated horseradish peroxidase in PBSTB was then added to each well, and the wells were incubated for 1 hour at room temperature. The plates were then washed and reacted with substrate solution (0.1% 3',3',5',5'-tetramethyl benzidine and 0.003% $H_2O_2$) for 30 minutes at room temperature. The reaction was terminated by adding of 50 µl of 2M sulphuric acid. The optical density was read at 450 nm.

The mAb BAT123 and G3-472 bind to an epitope in the PND. The mAb G3-519 binds to an epitope in the CD4 binding region (amino acid residue numbers 423–437). The mAb G3-136, whose binding epitope is unidentified as yet, competed with biotinylated G3-4 binding to gp120, but the antibodies BAT123, G3-519 and G3-472 did not.

7. Competitive ELISA of the Binding of Biotinylated Monoclonal Antibody to HIV-1B gp120 by Recombinant Soluble CD4 (sCD4)

A double-antibody capture ELISA was used as described earlier by Moore et al., *J. AIDS* 4:305–15 (1990). Wells of Immunlon 2 microtest plates were coated with 100 µl of affinity-purified sheep anti-HIV-1 gp120 antibodies (*International Enzymes, Inc.*, Fallbrook, Calif.) at 5 µg/ml in PBS for overnight at room temperature. The antibodies were raised against a synthetic peptide of the gp120 of the BH-10 strain of HIV-1 (amino acid residue numbers 497 to 511). The amino acid sequence of this peptidic segment is conserved among diverse HIV-1 strains. After incubation, the wells were blocked with 5% non-fat dry milk in PBS for 1 hour at room temperature. The plate was washed with PBST, 100 µl of 0.5 µg/ml purified HIV-1$_B$ gp120 in the blocking solution was added to each well for 2 hours at room temperature. The plate was washed. A total of 50 µl of serially diluted recombinant sCD4 (Biogen, 40 µg/ml to 40 ng/ml) in PBSTB and 50 µl of diluted biotinylated monoclonal antibodies (BAT123, G3-472, G3-4, G3-136 or G3-519) added to the corresponding wells for incubation for 1 hour at room temperature. For the control wells, only the biotinylated antibody was added. The working dilution of the antibody was determined to be within the linear range of its binding to gp120. The plate was then washed. 100 µl of diluted streptavidin-horseradish peroxidase in PBSTB was added to each well for reaction for 1 hour at room temperature. The plate was washed, and 200 µl of peroxidase substrate solution containing 0.1% 3',3',5',5'-tetramethyl benzidine and 0.003% $H_2O_2$ was added to each well for color development for 30 minutes. The reaction was stopped by addition of 50 µl of 2M $H_2SO_4$, and the OD was measured by a BioTek ELISA reader at 450 nm.

TABLE I

| | Specific Cell Binding (%) |
|---|---|
| biotinylated G3-4 alone (at 1:1000 dilution) | 23.4 |
| + 10 µg/ml chimeric BAT123 | 65.1 |
| + 10 µg/ml G3-472 | 66.0 |
| + 10 µg/ml G3-4 | 10.6 |
| + 10 µg/ml G3-136 | 6.4 |
| + 10 µg/ml G3-519 | 29.7 |
| + 10 µg/ml MOPC-21 (negative control) | 24.5 |
| biotinylated G3-136 alone (at 1:1000 dilution | 15.7 |
| + 10 µg/ml chimeric BAT123 | 48.6 |
| + 10 µg/ml G3-472 | 87.7 |
| + 10 µg/ml G3-4 | 10.1 |
| + 10 µg/ml G3-136 | 5.1 |
| + 10 µg/ml G3-519 | 17.1 |
| + 10 µg/ml MOPC-21 (negative control) | 15.0 |

C. CONCLUSIONS

G3-4 appeared to bind to a unique epitope on gp120, as determined by ELISA. Its binding is not inhibited by BAT123, which recognizes the PND, or by G3-519, which recognizes the CD4-binding domain (amino acid residue numbers 412–456). In fact, the binding of G3-4 and G3-136 to HIV-1 gp120 on the surface of H9 cells is enhanced by antibodies against the PND. In addition, the binding of G3-4 to gp120 can be inhibited by soluble CD4, suggesting that G3-4 recognizes a conformational epitope, as distinct from the putative CD4 binding domain recognized by G3-519, which is also involved in the interaction between the CD4 antigen and gp120.

Those skilled in the art will recognize, or be able to ascertain using no more than routine experimentation, many equivalents to the specific embodiments of the invention described herein. Such equivalents are intended to be encompassed by the following claims.

What is claimed is:

1. The monoclonal antibody which is produced by the hybridoma on deposit at the American Type Culture Collection under accession number HB 10733.

2. A hybridoma cell line which is on deposit at the American Type Culture Collection under accession number HB 10733.

3. An Fab, F(ab')$_2$, or Fv fragment of the monoclonal antibody of claim 1.

* * * * *